United States Patent [19]

Nedelec et al.

[11] Patent Number: 4,921,846
[45] Date of Patent: May 1, 1990

[54] NOVEL 17-HETERO SUBSTITUTED STEROIDS

[75] Inventors: Lucien Nedelec, Le Raincy; André Claussner, Villemomble; Daniel Philibert, La Varenne Saint-Hilaire; Martine Moguilewsky, Paris, all of France

[73] Assignee: Roussel Uclaf, Paris, France

[21] Appl. No.: 245,750

[22] Filed: Sep. 16, 1988

[30] Foreign Application Priority Data

Sep. 18, 1987 [FR] France ................ 87 12937

[51] Int. Cl.$^5$ .................. A61K 31/58; C07J 71/00
[52] U.S. Cl. .................. 514/173; 540/23
[58] Field of Search .................. 540/4, 23; 514/173

[56] References Cited

U.S. PATENT DOCUMENTS

| 3,364,207 | 1/1968 | Brown | 540/28 |
|---|---|---|---|
| 3,422,096 | 1/1969 | Brown | 540/45 |
| 4,233,296 | 11/1980 | Teutsch et al. | 514/172 |
| 4,536,401 | 8/1985 | Neef et al. | 514/173 |
| 4,540,686 | 9/1985 | Philibert et al. | 514/179 |
| 4,609,651 | 9/1986 | Rohde et al. | 514/179 |

FOREIGN PATENT DOCUMENTS 8200294 2/1982 PCT Int'l Appl. .................. 540/15

Primary Examiner—Joseph A. Lipovsky
Attorney, Agent, or Firm—Bierman and Muserlian

[57] ABSTRACT

Steroids with a 17-spiro substituent of 3,4 or 6 ring members of the formula

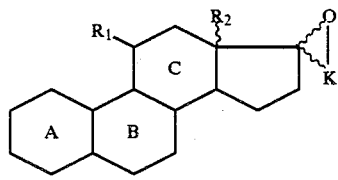

wherein $R_1$ is selected from the group consisting of carbocyclic aryl, heterocyclic aryl and aralkyl, $R_2$ is a hydrocarbon of 1 to 18 carbon atoms in the α- or β-position, the wavy line of the spiro ether indicates the oxygen is α- or β-, X is selected from the group consisting of —CH=CH—CH$_2$—CH$_2$— and —(CH$_2$)$_n$—, n is 1, 2 or 4, the A and B rings have a structure selected from the group consisting of

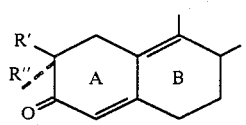 (a)

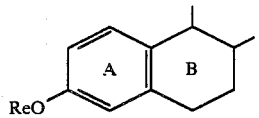

(b)

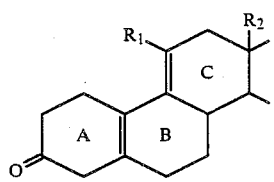

(c)

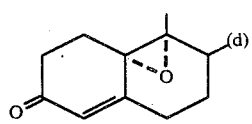

(d)

and

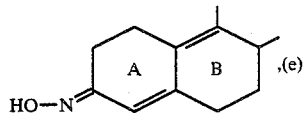 (e)

R' and R" are individually hydrogen or alkyl of 1 to 4 carbon atoms, $R_e$ is selected from the group consisting of hydrogen, alkyl of 1 to 6 carbon atoms, substituted alkyl of 1 to 6 carbon atoms and acyl and their non-toxic, pharmaceutically acceptable acid addition salts having a remarkable antiprogestomimetic activity.

22 Claims, No Drawings

NOVEL 17-HETERO SUBSTITUTED STEROIDS

STATE OF THE ART

Related steroids are described in published European patent application No. 116,974 and No. 156,284, U.S. Pat. No. 4,547,493 and copending application Ser. No. 138,847 filed Nov. 25, 1987.

OBJECTS OF THE INVENTION

It is an object of the invention to provide the novel steroids of formula I and their non-toxic, pharmaceutically acceptable salts and a novel process and novel intermediates for their preparation.

It is another object of the invention to provide novel antiprogestomimetic compositions and a novel method of inducing antiprogestomimetic activity in warm-blooded animals.

These and other objects and advantages of the invention will become obvious from the following detailed description.

THE INVENTION

The novel compounds of the invention are selected from the group consisting of steroids of the formula

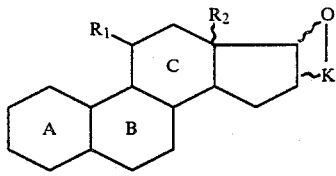

wherein $R_1$ is selected from the group consisting of optionally substituted carbocyclic aryl, heterocyclic aryl and aralkyl, $R_2$ is a hydrocarbon of 1 to 18 carbon atoms in the α- or β-position, the wavy line of the spiro ether indicates the oxygen is α- or β-, X is selected from the group consisting of —CH=CH—CH$_2$—CH$_2$— and —(CH$_2$)$_n$—, n is 1, 2 or 4, the A and B rings have a structure selected from the group consisting of

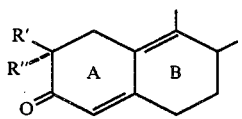

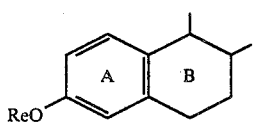

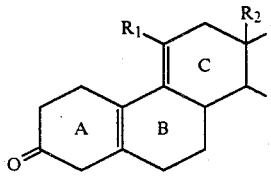

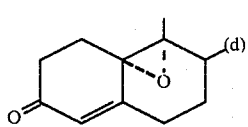

and

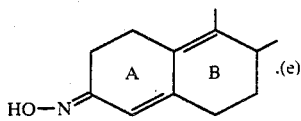

R' and R" are individually hydrogen or alkyl of 1 to 4 carbon atoms, $R_e$ is selected from the group consisting of hydrogen, alkyl of 1 to 6 carbon atoms, substituted alkyl of 1 to 6 carbon atoms and acyl and their non-toxic, pharmaceutically acceptable acid addition salts. When X is —CH$_2$—, R' and R" are preferably hydrogen.

When $R_1$ is an optionally substituted carbocyclic aryl or aralkyl, it is preferably a phenyl or benzyl which may be substituted in the ortho, meta or para position by at least one member of the group consisting of alkyl of preferably 1 to 8 carbon atoms, alkoxy of preferably 1 to 8 carbon atoms such as methoxy, ethoxy, propoxy, isopropoxy, butoxy, isobutoxy, tert-butoxy, alkenyloxy such as vinyloxy or allyloxy, all optionally substituted by at least one halogen such as fluorine, chlorine, bromine, iodine and preferably chlorine or fluorine; by at least one member chosen from the group consisting of hydroxyl, trifluoromethyl, acyl of 1 to 6 carbon atoms such as acetyl, propionyl, optionally esterified carboxy such as methoxy carbonyl, ethoxycarbonyl, propoxycarbonyl, alkylthio of 1 to 8 carbon atoms such as methylthio or ethylthio optionally oxidized in the form of sulfoxide or of sulfone; by at least one amino or amino mono- or disubstituted by alkyl of 1 to 8 carbon atoms, themselves optionally substituted such as methylamino, dimethylamino and bis (chloroethyl) amino, the amino or mono- or disubstituted amino optionally being oxidized into N-oxide, amino incorporated in a heterocycle optionally containing a heteroatom chosen from the group consisting of oxygen, nitrogen and sulfur such as morpholino or piperidinyl. The aryl or aralkyl can be substituted by a combination of these various radicals such as for example 2-methylthioethoxy, 3-fluoro, 4-dimethylamino. $R_1$ can also be a heterocyclic aryl optionally substituted by the various radicals considered above. The following can be cited: thienyl, furyl, isothienyl, isofuryl, thiazolyl, isothiazolyl, oxazolyl, isoxazolyl, thiadiazolyl, pyridinyl or piperidinyl and the heterocycles known to an expert.

As a substituent on the aryl nucleus, there can also be considered an amino-substituted alkyl such as one of the following radicals: dimethylaminomethyl, dimethylaminoethyl, methyl-(dimethylaminoethyl)-amino; amino-substituted alkoxy such as dimethylaminoethoxy. There can also be cited groups containing a silicon such as a trimethylsilyl phenyl. The previously cited radicals containing a nitrogen atom or a sulfur atom can be oxidized. Generally, the products in which $R_1$ contains a heteroatom, nitrogen or sulfur are preferred.

Examples of $R_1$ are:

-continued
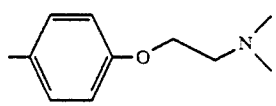
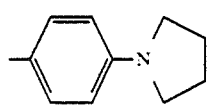
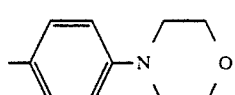
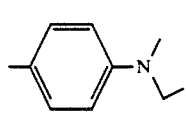
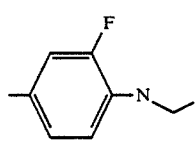
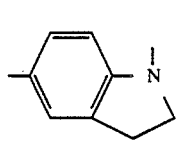
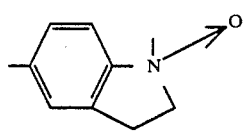
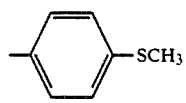
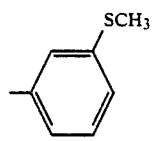
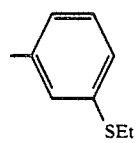
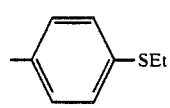
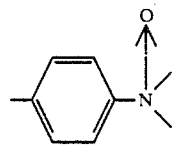
-continued
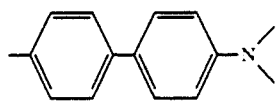
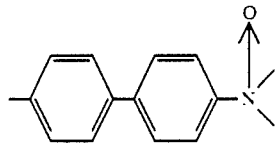
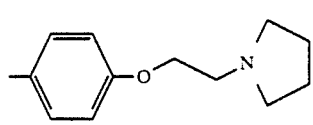
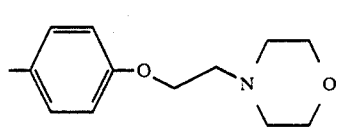
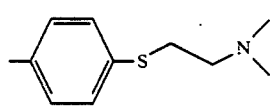
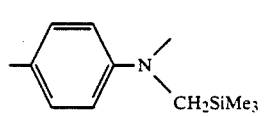
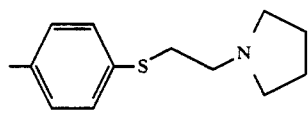
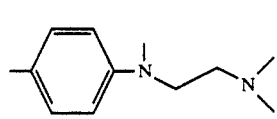
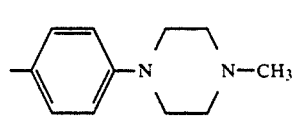
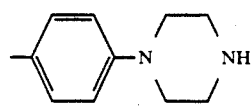
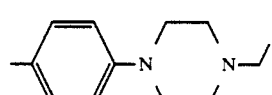
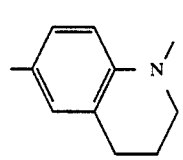

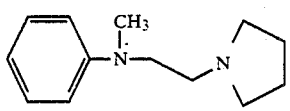
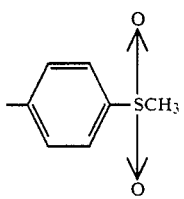
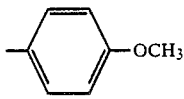
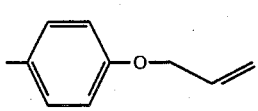
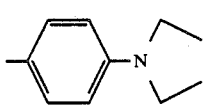
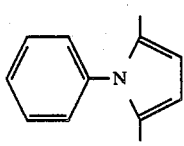
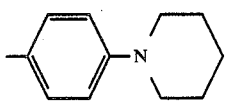
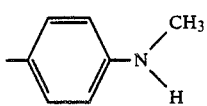
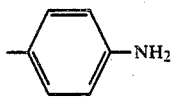
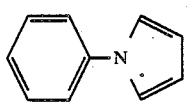
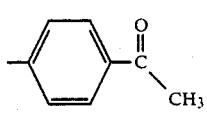
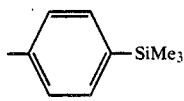

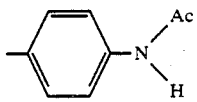
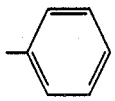
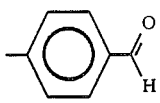

$R_2$ preferably is a saturated linear or branched alkyl of 1 to 4 carbon atoms such as methyl, ethyl, propyl or butyl. It is preferred for $R_2$ to be methyl or ethyl, especially methyl. $R_2$ can be in the $\alpha$ or $\beta$ position, preferably in the $\beta$ position. In the latter case, the oxygen atom of the spiro ether function is in the 17-$\beta$ position.

When $R_1$ contains a carboxy, it can be salified. Among the possible salts are the salts of the following: sodium, potassium, lithium, calcium, magnesium or ammonium. There can be cited, among the organic bases, methylamine, propylamine, trimethylamine, diethylamine, triethylamine, N,N-dimethylethanolamine, tris (hydroxymethyl) amino methane, ethanolamine, pyridine, picoline, dicyclohexyl amine, morpholine, benzylamine, procaine, lysine, arginine, histidine, N-methylglucamine.

When $R_1$ contains a function which can be salified by an acid, particularly an amino function, addition salts are obtained with acids.

The invention of course extends to the addition salts with acids of the salifiable compounds of formula I, such as, for example, the salts formed with one of the following acids: hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane or ethane sulfonic acid, arylsulfonic acids such as benzene or p-toluene sulfonic acid and arylcarboxylic acids.

Among the preferred products of formula I are those of the formula

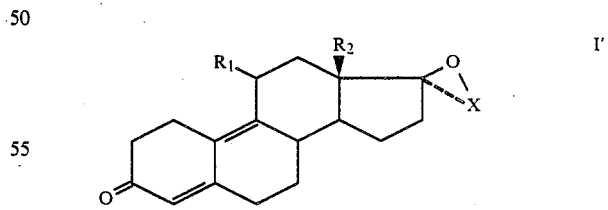

wherein $R_1$ is carbocyclic aryl or heterocyclic aryl or aralkyl all optionally substituted, $R_2$ in the beta-position is a hydrocarbon of 1 to 18 carbon atoms, the oxygen atom of the spiro ether is in 17-$\beta$, position X is —(CH$_2$)$_n$ and n is an integer 2 or 4 or X is —CH=CH—CH$_2$—CH$_2$—, as well as their salts. Among the products of formula I, the products are also preferred in which $R_1$ is either an aryl or an aralkyl carrying an amine function:

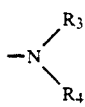

in which $R_3$ and $R_4$ individually is a primary, secondary or tertiary alkyl of 1 to 8 carbon atoms or $R_3$ and $R_4$ form together with the nitrogen atom to which they are linked a heterocycle optionally containing another heteroatom chosen from the group consisting of oxygen, nitrogen, sulfur and silicon, or aryl carrying a methylthio or ethylthio, as well as their salts.

Among the latter products cited, particularly the products of formula I are preferred in which $R_1$ is a phenyl, the substituent carried by this phenyl is in the para position, as well as their salts, as well as the products of formula I in which $R_1$ is selected from the group consisting of:

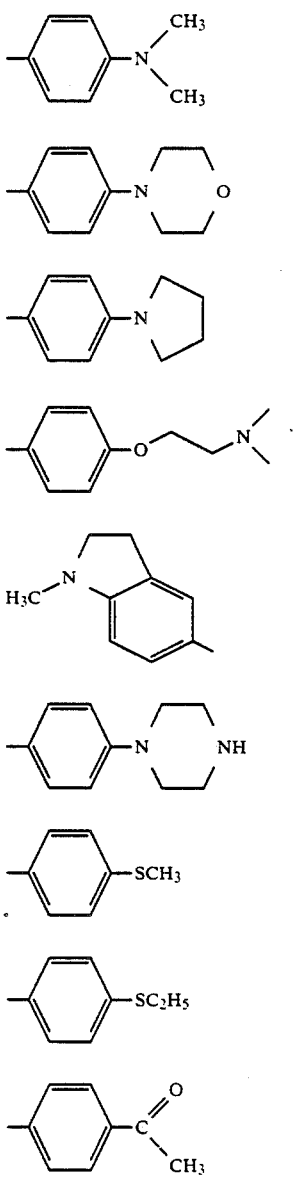

and

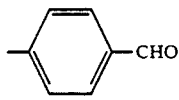

as well as their salts. $R_1$ is most preferably

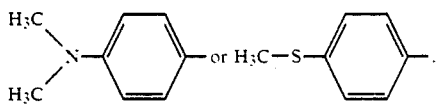

Specific preferred products of formula I are:
(17R) 11β-[4-(dimethylamino)-phenyl]-spiro ($\Delta^{4,9}$-estradien-17,2'-oxetan)-3-one and
(17R) 11β-[4-(methylthio)-phenyl]-spiro ($\Delta^{4,9}$-estradien-17,2'-oxetan)-3-one.

The novel process of the invention to prepare compounds of the formula

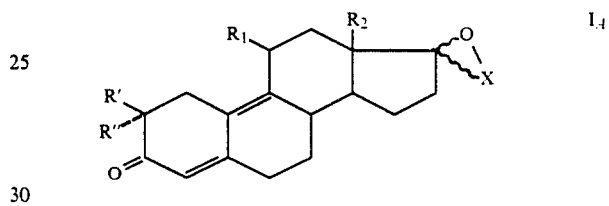

wherein $R_1$ and $R_2$ have the above definitions, R' and R'' are individually hydrogen or alkyl, or one is hydrogen and the other is alkyl comprises reacting a product of the formula

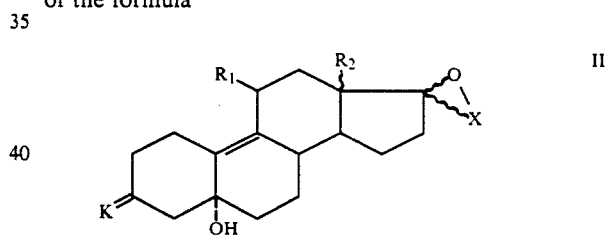

wherein K is a blocked ketone to the action of a dehydration reagent which is also capable of freeing the ketone function to obtain a compound of formula $I_A$ wherein R' and R'' are hydrogen and, if desired, reacting the products of formula $I_A$ wherein $R_1$ contains a sulfur or nitrogen with an oxidation agent to obtain the products in which $R_1$ contains a sulfur atom oxidized into sulfoxide or into sulfone or a nitrogen atom oxidized into N-oxide, and if desired, the products of formula $I_A$ are submitted to the action of a strong base, then to the action of an alkyl halide to obtain a product of formula $I_A$ in which R' and/or R'' is alkyl of 1 to 4 carbon atoms.

The process of the invention to prepare the products of the formula

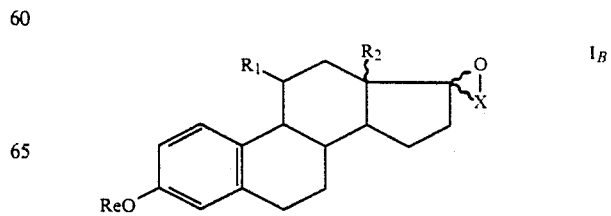

wherein $R_1$, $R_2$ and $R_e$ have the above definitions comprises reacting a product of the formula

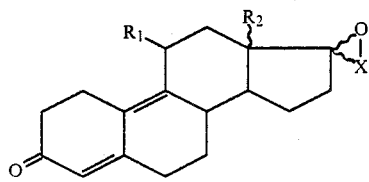

wherein $R_1$ and $R_2$ are as defined above with an aromatization agent, then if necessary or desired, to the action of a saponification agent and finally, if desired, the product of formula $I_B$ in which $R_e$ is hydrogen is submitted to an alkylation reagent.

The process of the invention to prepare the products of the formula

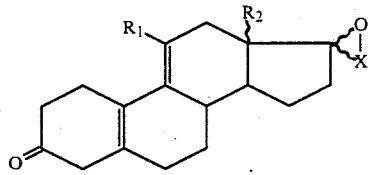

wherein $R_1$ and $R_2$ have the above definitions comprises reacting a product of formula $I_A'$ with an acylation agent and then a saponification agent to obtain a compound of the formula

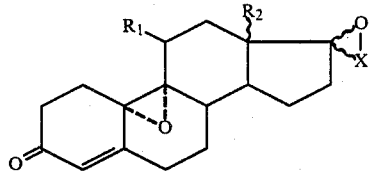

wherein X, $R_1$ and $R_2$ have the above definitions or reacting a product of formula $I_A'$ with an epoxidation agent to obtain a compound of the formula

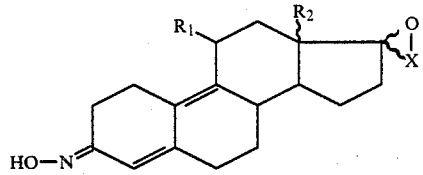

wherein X, $R_1$ and $R_2$ have the above definitions or reacting hydroxylamine with a compound of formula $I_A'$ and if necessary or desired, the products of formula $I_A$, $I_B$, $I_C$, $I_D$ and $I_E$ are salified.

In a preferred method of the above process, the conversion of the products of formula II by a dehydration reagent also capable of freeing the ketone function is effected preferably by a sulfonic resin in the acid form, for example, a commercial sulfonic resin with a polystyrene support or with a styrene/divinyl benzene polymer support. However, a mineral acid such as hydrochloric acid or sulfuric acid in a lower alkanol, or perchloric acid in acetic acid, or a sulfonic acid such as p-toluene sulfonic acid or potassium acid sulfate in a water/methylene chloride mixture may be used.

In the compounds of formula II, K is a ketal such as dimethylketal, dioxyethylene, 2,2-dimethyl-propan-1,3-dioxy or a corresponding thioketal, an oxime or a methyloxime.

The oxidation agent reacting with the compounds of formula $I_A$ or the epoxidation agent reacted to form the products of formula $I_D$ is preferably a peracid such as m-chloroperbenzoic acid, peracetic acid or perphthalic acid. Hydrogen peroxide can also be used by itself or in the presence of hexachloro- or hexafluoro-acetone. Depending on the number of functions which can be subjected to an oxidation, one or more equivalents of oxidizing agent can be used. Thus, for example, if it is desired to oxidize the sulfur atom contained by $R_1$ into sulfone, at least two equivalents of oxidizing agent must of course be used.

The strong base used on the products of formula $I_A$ can be an alkali metal amide such as sodium or lithium amide optionally prepared in situ and the alkyl halide used is preferably an iodide such as methyl iodide. The aromatization agent used to prepare the products of formula $I_B$ is preferably an acyl halide such as acetyl bromide or an acid anhydride such as acetic anhydride, or a mixture of the two. The optional acylation of the products of formula $I_B$ and the acylation leading to the products of formula $I_C$ are effected by the usual methods and an acyl halide is preferably used.

The optional alkylation of the products of formula $I_B$ is carried out by known methods, for example, with alkyl halide. The saponification agent used to obtain the products of formula $I_B$ or $I_C$ is preferably an alkaline base such as sodium or potassium hydroxide and the reaction is effected in a lower alcohol such as methanol or ethanol. Formation of oximes from the products of formula $I_A'$ is carried out using hydroxylamine in the form of a salt, preferably the hydrochloride in an alcohol at reflux.

The salification is carried out in standard conditions such as in the presence of ethanolic sodium hydroxide. An alkali metal salt can also be used such as sodium or potassium carbonate or sodium or potassium bicarbonate. Also, the salification by an acid is carried out in the usual conditions, preferably with hydrochloric acid, for example in an ether solution.

Also a subject of the invention is a process for the preparation of products of formula I as defined above in which X is $-(CH_2)_4-$ or $-CH=CH-CH_2-CH_2-$ comprising subjecting a compound of the formula

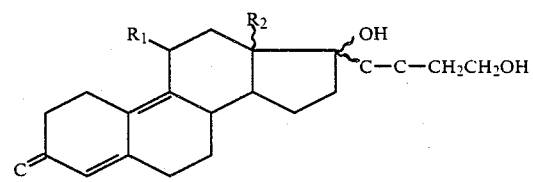

wherein $R_1$ and $R_2$ have the above definitions and the dotted line indicates the possible presence of a double bond between the carbons to the action of a cyclization reagent to obtain a product of the formula

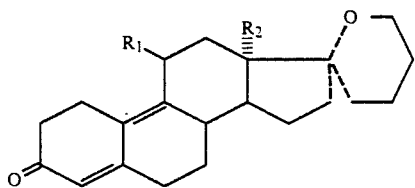

corresponding to a product of formula $I_4''$ in which R' and R'' are both hydrogen and X is —(CH$_2$)$_4$— and —CH=CH—CH$_2$—CH$_2$—, which products of formula $I_4''$ are converted into the corresponding products of formula $I_4$ in which one of the R' or R'' or both are alkyl of 1 to 4 carbon atoms, and into products of formulae $I_B$, $I_C$, $I_D$ and $I_E$ by the process described above.

In a preferred method of the said process, the cyclization reagent which is preferably reacted with the products of formula III is tosyl chloride in the presence of pyridine but there can also be used methylsulfonyl chloride.

The novel antiandrogenic composition of the invention are comprised of an antiandrogenically effective amount of at least one compound of formula I and their non-toxic, pharmaceutically acceptable salts and an inert pharmaceutical carrier or excipient. The compositions may be in the form of tablets, dragees, gelules, granules, suppositories, ointments, creams, gels and injectable preparations.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting agents, dispersants and emulsifiers and preservatives.

The compositions also possess an antigulucocorticoid activity as shown by the results in the tests hereafter. Moreover, some of the products show an antiprogestomimetic acitivity which is greater than their anti-glucocorticoid property.

The products of formula I as well as their pharmaceutically acceptable salts which possess antiprogestomimetic properties can be used as contraceptives and against hormone irregularities. Some products of formula I as well as their pharmaceutically acceptable salts also have progestomimetic properties and can be employed in the treatment of amenorrhea, dysmenorrhea and luteal insufficiencies.

The products of formula I as well as their pharmaceutically acceptable salts can therefore be used as medicaments mainly for combating side-effects of glucocorticoids and also enable the combating of disorders due to a hyper-secretion of glucocorticoids and particularly the combatting of ageing in general and more particularly of hypertension, atherosclerosis, osteoporosis, diabetes, obesity as well as immuno-depression and insomnia.

The products of formula I as well as their pharmaceutically acceptable salts which offer antiandrogen properties can be used in the treatment of hypertrophies and of cancer of the prostate, of hyperandrogeny, of anaemia, of hirsutism and of acne. The products of formula I as well as their pharmaceutically acceptable salts also possess antiproliferative properties which make them of use in the treatment of hormone-dependent cancers, particularly mammary carcinomas and their metastases.

These properties also make them of use in the treatment of benign tumors.

Some of the products of formula I as well as their pharmaceutically acceptable salts possess estrogenic and/or anti-estrogenic properties. The anti-estrogenic properties make them of use in the treatment of estrogeno-dependent cancers. The estrogenic properties which can also be offered by the said products of formula I as well as their pharmaceutically acceptable salts also make them useful in the treatment of disorders connected with a hypofolliculinemia, for example amenorrhea, dysmenorrhea, repeated miscarriages, pre-menstrual disorders as well as in the treatment of the menopause.

The method of the invention of inducing antiandrogenic activity in warm-blooded animals, including humans, comprises adminstering to warm-blooded animals an antiandrogenically effective amount of at least one compound of formula I and their non-toxic, pharmaceutically acceptable salts. The compounds may be administered parenterally, orally, rectally or topically. The usual oral daily dose is 0.13 to 13.3 mg/kg depending on the condition treated, the method of administration and the specific compound.

The novel intermediates of the invention are compounds of the formula

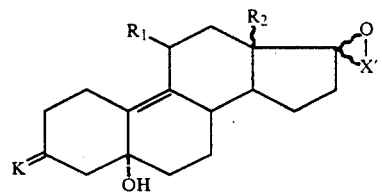

wherein $R_1$, $R_2$ and K have the above definitions and X' is —(CH$_2$)$_{nl}$—, nl is 2 or 4, or X' is —CH=CH—CH$_2$—CH$_2$—. The products of formula II' can be prepared by cyclization of the corresponding products of the formula

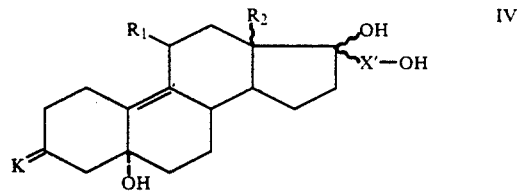

wherein X' is —(CH$_2$)$_{nl}$—, nl=2 or 4 or X' is —CH=CH—CH$_2$—CH$_2$—.

The products of formula IV can themselves be prepared starting from products of the formula

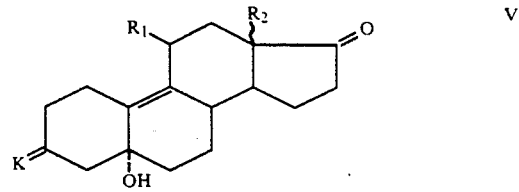

by reaction with derivatives of H—C≡C—(CH$_2$)$_2$OH or CH$_3$CO$_2$Alk in the presence of a strong base, (Alk=alkyl of C$_{1-4}$) followed if necessary by a separation of the isomeric mixtures by the usual methods such as chromatography.

The products obtained in which ring D has the following structure:

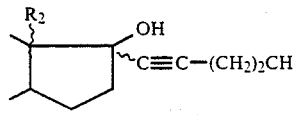 (1)

or

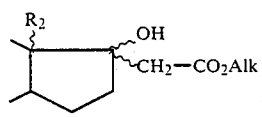 (2)

are submitted to a partial or total hydrogenation for the primary products 1 to obtain the products of formula IV in which X' is —CH=CH—CH$_2$—CH$_2$— or —(CH$_2$)$_{nl}$— in which nl is 4. The products of formula 2 are submitted to a reducing reagent to obtain the products of formula IV in which X' is —(CH$_2$)$_2$—.

The products of formula II in which X is —(CH$_2$)$_2$— can be prepared by the action of a trimethyl sulfonium halide on the products of formula V in the presence of a strong base. Some methods of preparation for products of this type are found in European Patent EP No. 0,192,598.

The products of formula II' can also be prepared by reacting a product of the formula

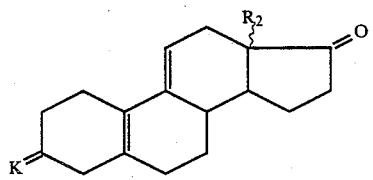 VI with either a product of the formula H—C≡C—(CH$_2$)$_2$OH to obtain a product having the same ring D as product 1 above and then the product is submitted to a partial or total hydrogenation reaction or with a product of the formula: CH$_3$CO$_2$Alk to obtain a product having the same ring D as product 2 above and then this product is submitted to a reducing agent to obtain a product of the formula

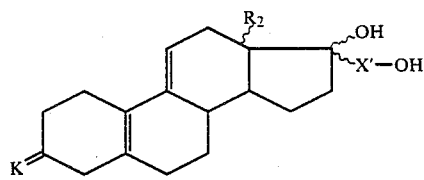 VII in which K, X' and R$_2$ have the above definitions, and the products of formula VII are submitted to a cyclization agent to obtain a product of the formula

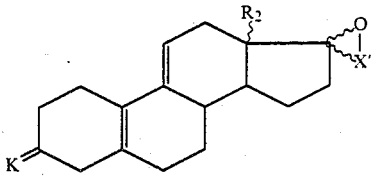 VIII in which K, R$_2$ and X' have the above definitions, which is submitted to an epoxidation reagent to obtain a product of the formula

IX and reacting the latter with a reagent chosen from the group consisting of (R$_1$)$_2$CuLi, R$_1$MgHal in the presence of cuprous or cupric salts and (R$_1$)$_2$CuCNLi$_2$ to obtain the expected products of formula II'.

In a preferred method of carrying out the said process, the agent which cyclizes the products of formula IV into products of formula II' is toluene sulfonyl chloride or methane sulfonyl chloride in pyridine.

The reaction of the product of the formula H—C≡C—(CH$_2$)$_2$OH with the product of formula V is carried out preferably in the presence of potassium tert-butylate or of butyl or methyl lithium in a solvent such as tetrahydrofuran. The reaction of the product of the formula CH$_3$CO$_2$Alk in which Alk is preferably tert-butyl is carried out preferably in the presence of lithium diisopropylamide in a solvent such as tetrahydrofuran.

The total hydrogenation of the product 1 is carried out for example by a mixture of methanol and palladium on charcoal or by chlorotristriphenyl phosphino rhodium in benzene or a benzene/ethanol mixture and passage of hydrogen. The partial hydrogenation can be carried out by hydrogen in the presence of palladium on barium sulfate poisoned by an amine such as quinoline or triethylamine in a solvent such as ethyl acetate. The reduction of the products 2 can be carried out preferably with lithium aluminum hydride, for example, in tetrahydrofuran.

The formation of the epoxide in position 17,20 is carried out preferably by the action of trimethylsulfonium iodide in the presence of potassium tert-butylate in a solvent or a mixture of solvents such as tetrahydrofuran and dimethylsulfoxide.

The products of formula III can be prepared by the action, on the previously cited products of formula IV, of a dehydration reagent also capable of freeing the ketone function which is chosen from the reagents cited above and in particular dilute acetic acid or hydrochloric acid in methanol. This reaction can in addition be carried out starting with the products 1 above without isolation of the product IV, the partial or total hydrogenation reaction of the products 1 being followed by the deprotection reaction of the ketone function.

The epoxidation reaction used to convert the products of formula VIII into products of formula IX is hydrogen peroxide in hexafluoroacetone and the undesired beta isomer is separated by chromatography. The reagent which is preferably made to react with the product of formula IX is $R_1MgBr$ in the presence of cuprous chloride.

Examples of compounds of the formula

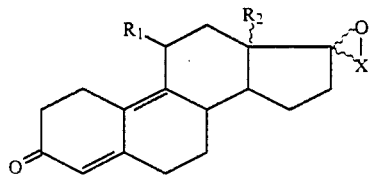

in which $R_1$, $R_2$ and X have the following value and the oxygen atom of the spiro ether is in the 17 beta-position are in the following Table.

| $R_1$ | $R_2$ | X |
|---|---|---|
| phenyl | β CH₃ | —CH₂ |
| " | " | (CH₂)₂ |
| " | " | (CH₂)₄ |
| " | " | CH=CH—CH₂—CH₂ |
| 4-methylphenyl | " | —CH₂ |
| " | " | (CH₂)₂ |
| " | " | (CH₂)₄ |
| " | " | CH=CH—CH₂—CH₂ |
| 3-methylphenyl | " | —CH₂ |
| " | " | (CH₂)₂ |
| " | " | (CH₂)₄ |
| " | " | CH=CH—CH₂—CH₂ |
| 2-methylphenyl | " | —CH₂ |
| " | " | (CH₂)₂ |
| " | " | (CH₂)₄ |
| " | " | CH=CH—CH₂—CH₂ |
| 4-chlorophenyl | " | —CH₂ |
| " | " | (CH₂)₂ |
| " | " | (CH₂)₄ |
| " | " | CH=CH—CH₂—CH₂ |
| 3-chlorophenyl | " | —CH₂ |
| " | " | (CH₂)₂ |
| " | " | (CH₂)₄ |
| " | " | CH=CH—CH₂—CH₂ |

-continued

| $R_1$ | $R_2$ | X |
|---|---|---|
| 2-chlorophenyl | " | —CH₂ |
| " | " | (CH₂)₂ |
| " | " | (CH₂)₄ |
| " | " | CH=CH—CH₂—CH₂ |
| 4-aminophenyl | " | —CH₂ |
| " | " | (CH₂)₂ |
| " | " | (CH₂)₄ |
| " | " | CH=CH—CH₂—CH₂ |
| 3-aminophenyl | " | —CH₂ |
| " | " | (CH₂)₂ |
| " | " | (CH₂)₄ |
| " | " | CH=CH—CH₂—CH₂ |
| 4-(dimethylamino)phenyl | β C₂H₅ | —CH₂ |
| " | " | (CH₂)₂ |
| " | " | (CH₂)₄ |
| " | " | CH=CH—CH₂—CH₂ |
| " | α CH₃ | —CH₂ |
| " | " | (CH₂)₂ |
| " | " | (CH₂)₄ |
| " | " | CH=CH—CH₂—CH₂ |
| 3-(methylamino)phenyl | β CH₃ | —CH₂ |
| " | " | (CH₂)₂ |
| " | " | (CH₂)₄ |
| " | " | CH=CH—CH₂—CH₂ |
| 4-methoxyphenyl | " | —CH₂ |
| " | " | (CH₂)₂ |
| " | " | (CH₂)₄ |
| " | " | CH=CH—CH₂—CH₂ |
| 4-isopropoxyphenyl | " | —CH₂ |

-continued

| R₁ | R₂ | X |
|---|---|---|
| " | " | (CH₂)₂ |
| " | " | (CH₂)₄ |
| " | " | CH=CH—CH₂—CH₂ |
| 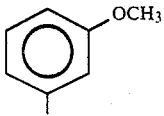 | " | —CH₂ |
| " | " | (CH₂)₂ |
| " | " | (CH₂)₄ |
| " | " | CH=CH—CH₂—CH₂ |
| 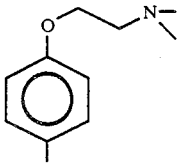 | " | —CH₂ |
| " | " | (CH₂)₂ |
| " | " | (CH₂)₄ |
| " | " | CH=CH—CH₂—CH₂ |
| 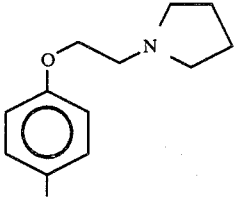 | " | —CH₂ |
| " | " | (CH₂)₂ |
| " | " | (CH₂)₄ |
| " | " | CH=CH—CH₂—CH₂ |
| 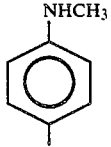 | " | —CH₂ |
| " | β-CH₃ | —CH₂ |
| " | " | (CH₂)₂ |
| " | " | CH=CH—CH₂—CH₂ |
| " | " | —CH₂ |
| 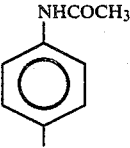 | " | |
| " | " | (CH₂)₂ |

-continued

| R₁ | R₂ | X |
|---|---|---|
| " | " | (CH₂)₄ |
| " | " | —CH₂ |
| 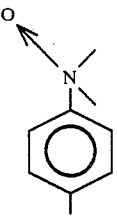 | " | |
| " | " | (CH₂)₂ |
| " | " | (CH₂)₄ |
| " | " | CH=CH—CH₂—CH₂ |
| 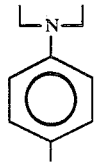 | " | —CH₂ |
| " | " | (CH₂)₂ |
| " | " | (CH₂)₄ |
| " | " | CH=CH—CH₂—CH₂ |
| 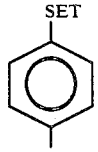 | " | —CH₂ |
| " | " | (CH₂)₂ |
| " | " | (CH₂)₄ |
| " | " | CH=CH—CH₂—CH₂ |
|  | " | —CH₂ |
| " | " | (CH₂)₂ |
| " | " | (CH₂)₄ |
| " | " | —CH₂ |
| 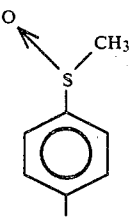 | " | |
| " | " | (CH₂)₂ |
| " | " | (CH₂)₄ |
| " | " | CH=CH—CH₂—CH₂ |

4,921,846

-continued

| R₁ | R₂ | X |
|---|---|---|
| 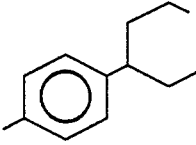 | " | —CH₂ |
| " | " | (CH₂)₂ |
| " | " | (CH₂)₄ |
| " | " | CH=CH—CH₂—CH₂ |
| 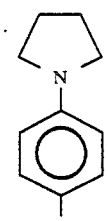 | p-CH₃ | —CH₂ |
| " | " | (CH₂)₂ |
| " | " | (CH₂)₄ |
| " | " | CH=CH—CH₂—CH₂ |
| 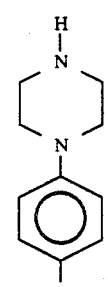 | " | —CH₂ |
| " | " | (CH₂)₂ |
| " | " | (CH₂)₄ |
| " | " | CH=CH—CH₂—CH₂ |
| 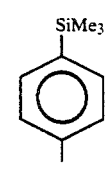 | " | —CH₂ |
| " | " | (CH₂)₂ |
| " | " | (CH₂)₄ |
| " | " | CH=CH—CH₂—CH₂ |
| 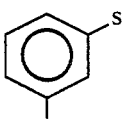 | " | —CH₂ |
| " | " | (CH₂)₂ |
| " | " | (CH₂)₄ |
| " | " | CH=CH—CH₂—CH₂ |
| 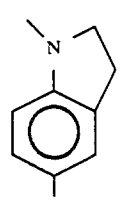 | " | —CH₂ |
| " | " | (CH₂)₂ |

-continued

| R₁ | R₂ | X |
|---|---|---|
| " | " | (CH₂)₄ |
| " | " | CH=CH—CH₂—CH₂ |
|  | " | —CH₂ |
| " | " | (CH₂)₂ |
| " | " | (CH₂)₄ |
| " | " | CH=CH—CH₂—CH₂ |
|  | " | —CH₂ |
| " | " | (CH₂)₂ |
| " | " | (CH₂)₄ |
| " | " | CH=CH—CH₂—CH₂ |
|  | " | —CH₂ |
| " | " | (CH₂)₂ |
| " | " | (CH₂)₄ |
| " | " | CH=CH—CH₂—CH₂ |
|  | " | —CH₂ |
| " | " | (CH₂)₂ |
| " | " | (CH₂)₄ |
| " | " | CH=CH—CH₂—CH₂ |
|  | " | —CH₂ |
|  | " | |
| " | " | (CH₂)₂ |
| " | " | (CH₂)₄ |

-continued

| R₁ | R₂ | X |
|---|---|---|
| " | " | CH=CH—CH₂—CH₂ |
| " | " | —CH₂ |
| 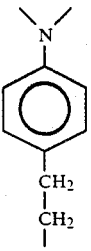 | " | (CH₂)₂ |
| " | " | (CH₂)₄ |
| " | " | CH=CH—CH₂—CH₂ |
| 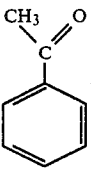 | " | —CH₂ |
| " | " | (CH₂)₂ |
| " | " | (CH₂)₄ |
| " | " | CH=CH—CH₂—CH₂ |
| 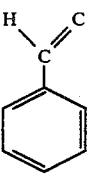 | " | —CH₂ |
| " | " | (CH₂)₂ |
| " | " | (CH₂)₄ |
| " | " | CH=CH—CH₂—CH₂ |
| 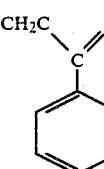 | " | —CH₂ |
| " | " | (CH₂)₂ |
| " | " | (CH₂)₄ |
| " | " | CH=CH—CH₂—CH₂ |

In the following examples there are described several preferred embodiments to illustrate the invention. However, it should be understood that the invention is not intended to be limited to the specific embodiments.

EXAMPLE 1

(17R) 11β-[4-(dimethylamino)-phenyl]-spiro (Δ⁴,⁹-estra-dien-17,2′-oxetan)-3-one

STEP A: (1,1-dimethyl ethyl) 3,3-[(1,2-ethanediyl)-bis oxy]-19-nor 17α-Δ⁵⁽¹⁰⁾,⁹⁽¹¹⁾-pregnadien-17β-ol-21-oate A solution of 568 ml of lithium diisopropylamide titrating 0.51M in 1.4 liters of tetrahydrofuran was cooled to −73° C. and over 20 minutes at −73° C. to −72° C., 37.3 ml of tert-butyl acetate were introduced. The mixture was stirred for one hour at −73° C. and the temperature was allowed to rise −60° C. 17.38 g of cyclic 3,3-(1,2-ethanediyl) acetal of Δ⁵⁽¹⁰⁾,⁹⁽¹¹⁾-estradien-3,17-dione in 260 ml of tetrahydrofuran were introduced over 30 minutes and the mixture was stirred for 80 minutes at −60° C.

The temperature of the medium is raised to 0° C. and, over 15 minutes, 520 ml of saturated aqueous ammonium chloride solution were added. After stirring for one hour at ambient temperature and decanting, the aqueous phase was extracted with methylene chloride. The organic phases were washed with a saturated aqueous sodium chloride solution, dried and evaporated to dryness. The residue was chromatographed on silica and eluted with a cyclohexane-ethylacetate-triethylamine mixture 95-5-0.001 to obtain 20.3 g of expected product.

NMR Spectrum (CDCl₃+1 drop C₅D₅N)
3.97 ppm: H ethylene dioxy in 3
5.6 ppm: H₁₁
0.9 ppm: H₁₈
4.55 ppm: OH
1.47 ppm: H of tBu Lithium diisopropylamide was prepared according to House et al J. Org. Chem., Vol. 43, p. 704 (1978) from 68 ml of diisopropylamine to obtain the expected product in solution with a titer of 0.51M.

STEP B: Cyclic (1,2-ethanediyl) acetal of 19-nor-17α-Δ⁵⁽¹⁰⁾,⁹⁽¹¹⁾-pregnadien-17β-,21-diol-3-one 20.3 g of the product of Step A, dissolved in 400 ml of tetrahydrofuran under inert atmosphere, were admixed with 14.38 g of lithium aluminum hydride over 5 minutes at +18° C. to +22° C. The mixture was heated to 40° C. for one hour, and after cooling to +15° C. to +20° C., 600 ml of methylene chloride were added. The mixture was rinsed at 0° C. to +5° C. and 130 ml of saturated aqueous sodium bicarbonate solution were slowly added. The precipitate was filtered and washed by trituration with methylene chloride. The filtrate was decanted and the aqueous phase was extracted with methylene chloride. The combined organic phases were washed with a saturated aqueous sodium chloride solution, dried and evaporated to dryness. The residue was triturated with ether, separated and dried under reduced pressure to obtain 12.47 g of the expected product.

NMR Spectrum (CDCl₃+1 drop C₅D₅N)
3.96 ppm: H of ethylene dioxy
5.59 ppm: H₁₁
0.88 ppm: H₁₈
3.97 ppm: H₂₁
3.33 ppm: H of OH STEP C: (17R) cyclic (1,2-ethanediyl) acetal of spiro (Δ⁵⁽¹⁰⁾,⁹⁽¹¹⁾-estradien-17,2′-oxetan)-3-one 12.47 g of the product of Step B were dissolved in 250 ml of pyridine and little by little, 24.94 g of tosyl chloride were added. The mixture was stirred for two hours at ambient temperature and ice and water were added. Extraction was carried out with ethyl acetate and the organic phases were washed with a saturated aqueous sodium chloride solution, dried further dried by entrainment with toluene. The 19.80 g of tosylate obtained were suspended in 890 ml of potassium hydroxide with 5% ethanol and stirred at reflux for 40 minutes. The ethanol was distilled off under reduced pressure, water and ice were added and the mixture was stirred for 10 minutes. The precipitate was separated, washed with water until neutral and dissolved in methylene chloride. The water was decanted and the residue was brought to dryness. The residue was chromatographed on silica (eluent: cyclohexane-ethyl acetate-triethylamine 90-10-0.001) to obtain 8.97 g of the expected product melting at 136° C.
NMR Spectrum (CDCl$_3$)
3.99 ppm: H of ethylene dioxy
5.64 ppm: H$_{11}$
0.76 ppm: H$_{18}$
4.30 to 4.50 ppm: H$_{21}$ STEP D: Epoxy isomer of 5β,10β-(17R) cyclic (1,2-ethanediyl)-acetal of 5α,10α-epoxy spiro (Δ$^{5,10),9(11)}$-estradien-17,2'-oxetan)-3-one The 8.97 g of the product of Step C were dissolved in 180 ml of methylene chloride and 9 ml of hexachloroacetone were added. The mixture was cooled to −30° C. and 27 ml of 50% hydrogen peroxide were introduced over 15 minutes at −33° C. to −31° C. The mixture was stirred for 3 hours at 0° C. to +2° C. and the mixture was poured into 300 ml of a saturated sodium bicarbonate solution. Sodium thiosulfate was added at +15° C. to +20° C. until there were no peroxide left and after decanting, the aqueous phase was extracted with methylene chloride. The organic phases were washed with water and with saturated aqueous sodium chloride solution, dried and evaporated to dryness. The residue was chromatographed on silica (eluent: cyclohexane-ethyl acetate-triethylamine 80-20-0.001) to obtain 1.82 g of the 5β, 10β-epoxy product and 5.36 g of the 5α, 10α-epoxy isomer.

| IR Spectrum (CHCl$_3$) |
| --- |
| α-epoxy: 973 cm$^{-1}$ |
| : 823 cm$^{-1}$ |
| β-epoxy: 981 cm$^{-1}$ |
| : 830 cm$^{-1}$ |
| NMR Spectrum (CDCl$_3$) |
| α-epoxy: 0.76 H$_{18}$ |
| 3.92 ppm ketal |
| 6.09 ppm H$_{11}$ |
| 4.30 to 4.46 ppm H$_{21}$ |
| β-epoxy: 0.75 ppm H$_{18}$ |
| 3.91 ppm ketal |
| 5.92 ppm H$_{11}$ |
| 4.30 to 4.46 ppm H$_{21}$ |

STEP E: (17R) cyclic (1,2-ethanediyl)-acetal of 11β-[-4-(dimethylamino)-phenyl]-spiro-(Δ$^9$estren-5α-ol-17,2'-oxetan)-3-one 0.861 g of the 5α-,10α-epoxide of Step D were dissolved in 18 ml of tetrahydrofuran under an inert atmosphere and 24 mg of cuprous chloride were added. After cooling to 0° C. to +5° C., 8.3 ml of 4-dimethylaminophenyl magnesium bromide in solution (0.877) in tetrahydrofuran were introduced over thirty minutes. The mixture was stirred for one hour at this temperature and was then poured at +15° C. to +20° C. into 40 ml of a saturated aqueous ammonium chloride solution. After stirring for 10 minutes and decanting, the aqueous phase was extracted with ethyl acetate. The organic phases were washed with a saturated sodium chloride solution, dried and evaporated to dryness. The residue was chromatographed on silica (eluent:cyclohexaneethyl acetate-triethylamine 70-30-0.001) to obtain 1 g of the expected product melting at 178° C.
NMR Spectrum (CDCl$_3$):
4.00 ppm: H ethylene dioxy
2.91 ppm: H dimethylamino 4.28 to 4.45 ppm: H$_{11}$ and H$_{21}$
0.40 ppm: H$_{18}$
4.31 ppm: OH STEP F: (17R) 11β-[4-(dimethylamino)-phenyl]-spiro-(Δ$^{4,9}$-estradien-17,2'-oxetan)-3-one 0.944 g of the product of Step E were dissolved in 6.6 ml of 70% acetic acid, heated to 41° C. to 43° C. and stirred for 135 minutes. After cooling to 0° C. to +5° C., ammonia was added to give a pH greater than 8, and extraction was carried out with methylene chloride. The extracts were washed with a saturated sodium chloide solution and evaporated to dryness. The residue was chromatographed on silica (eluent:cyclohexane-ethyl acetate 80-20) to obtain 0.468 g of the expected product. After crystallization from isopropanol, the product melted at 108° C.

| IR Spectrum (CHCl$_3$): |
| --- |
| conjugated ketone: 1654 cm$^{-1}$ |
| C=C: 1612 cm$^{-1}$ |
| Aromatic: 1561 cm$^{-1}$ |
| UV Spectrum (EtOH): |
| Max. 260 nm ε = 17,400 |
| Max. 302 nm ε = 20,500 |
| EtOH HCl 0.1 N |
| Max. 300 nm ε = 18,900 |
| Infl. 218–240 nm |
| NMR Spectrum (CDCl$_3$) |
| 2.92 ppm: H dimethylamino |
| 5.76 ppm: H$_4$ |
| 0.48 ppm: H$_{18}$ |
| 4.40 ppm: H$_{11}$ and H$_{21}$ |
| 6.67 ⎱ aromatics |
| 7.07 ⎰ |

EXAMPLE 2

(17R) 11β-[4-(methylthio)-phenyl]-spiro-(Δ$^{4,9}$-estradient-17,2'-oxetan)-3-one STEP A: (17R) cyclic (1,2-ethanediyl)-acetal of 11β-[4-(methylthio)-phenyl]-spiro-(Δ$^9$-estren-17,2'-oxetan)-5α-ol-3-one 55.3 ml of 4-(methylthio)-phenyl magnesium in tetrahydrofuran (titer 0.81M) and 0.148 g of cuprous chloride were cooled to 0° C. to +5° C. for 15 minutes under an inert atmosphere and 5.36 g of (17R) cyclic (1,2-ethanediyl) acetal of 5α-,10α-epoxy spiro-(Δ$^{5(10),9(11)}$-estradien-17,2'-oxetan)-3-one in 53 ml of tetrahydrofuran were introduced over 25 minutes at +3.5° C. to +5° C. and the mixture was agitated at 0° C. to +5° C. for one hour and a half. The operation was carried out as in Step E of Example 1 to obtain 0.24 g of the expected product.

| NMR Spectrum (CDCl$_3$) | |
| --- | --- |
| 2.46 ppm: | H$_3$C—S |
| 3.9 to 4.1 ppm: | H ethylene dioxy |
| 0.38 ppm: | H$_{18}$ |
| 4.30 to 4.45 ppm: | H$_{11}$, H$_{21}$ and OH |

| NMR Spectrum (CDCl$_3$) | |
|---|---|
| 7.16 ppm: | aromatics |

STEP B: (17R)
11β-[4-(methythio)-phenyl]-spiro-(Δ$^{4,9}$-estradien-17,2'-oxetan)-3-one 2 g of the product of Step A were dissolved in 40 ml of ethanol and after 2 g of Amberlite IRC 84 resin were added, the mixture was refluxed for 7 hours under an inert atmosphere. At ambient temperature, the mixture of resin and products was separated, rinsed with ethanol and with methylene chloride. The filtrate was evaporated to dryness to obtain 1.194 g of the expected product melting at 154° C. After two crystallization from 99.8% ethanol, the product melted at 160° C.

IRA Spectrum (CHCl$_3$)
C=O: 1653 cm$^{-1}$
C=C: 1603 cm$^{-1}$ aromatics $\begin{cases} 1556 \text{ cm}^{-1} \\ 1493 \text{ cm}^{-1} \end{cases}$ UV Spectrum (EtOH)
Max. 260 nm ε = 16,500
Max. 300 nm ε = 20,100

NMR Spectrum (CDCl$_3$):
5.77 ppm: H$_4$
2.46 ppm: S-CH$_3$
0.44 ppm: H$_{18}$
4.3 to 4.5 ppm: H$_{21}$ 7.12 ppm $\Big\}$ aromatics
7.18 ppm

EXAMPLE 3
(17S) 11β-[4-(dimethylamino)-phenyl]-3',4',5',6'-tetrahydro spiro (Δ$^{4,8}$-estradien-17,2'-(2H) pyran)-3-one STEP A: Cyclic (1,2-ethanediyl)-acetal of 11β-[4-(dimethylamino)-phenyl]-17α-(4-hydroxy 1-butynyl)-Δ$^9$-estrene-5α,17β-diol-3-one 5 g of potassium tert-butylate were dissolved in 20 ml of anhydrous tetrahydrofuran and, after cooling to −5° C., 1.9 g of cyclic (1,2-ethanediyl)-acetal of 11β-[4-(dimethylamino)-phenyl]-Δ$^9$-estrene-5-ol-3-one were introduced over 5 minutes. After stirring for 10 minutes, a solution of 2.4 ml of 3-butynol in 20 ml of tetrahydrofuran was introduced over 15 minutes and the mixture was poured into 200 ml of a saturated monosodium phosphate solution. Then, the aqueous phase was extracted with methylene chloride, dried and evaporated to dryness. The residue was purified on silica and eluted first with a cyclohexane-ethyl acetate mixture (1—1), and then with ethyl acetate with 1% of ammonia to obtain 1.775 g of the expected product.

NMR Spectrum (CDCl$_{36}$+1 drop C$_5$D$_5$N)
2.90 ppm: H of dimethylamino 3.97 ppm: H ethylene dioxy 0.5 ppm: H$_{18}$
3.73 ppm: CH$_2$-OH 6.62 and 7.04 ppm: aromatics

STEP B:
11β-[4-(dimethylamino)-phenyl]-17α-(4-hydroxy-butyl)-Δ$^{4,9}$-estradien-17β-ol-3-one 871 mg of the product of Step A were hydrogenated in 40 ml of methanol in the presence of 0.4 g of palladium-charcoal. After filtration and elimination of the solvents, the residue was taken up in 10 ml of 10% acetic acid and stirred for one hour at 45° C. After neutralizing with a saturated aqueous sodium bicarbonate solution, extraction was carried out with methylene chloride. The organic phase was dried and evaporated to dryness under reduced pressure. The residue was chromatographed on silica and eluted with ethyl acetate tof obtain 640 mg of the expected product.

IR Spectrum (CHCl$_3$)
C=O    1654 cm$^{-1}$

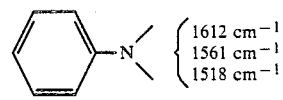 $\begin{cases} 1612 \text{ cm}^{-1} \\ 1561 \text{ cm}^{-1} \\ 1518 \text{ cm}^{-1} \end{cases}$ OH    3615 cm$^{-1}$
NMR Spectrum (CDCl$_3$):

2.9 ppm 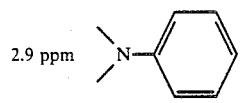

4.33 ppm: H$_{11}$
0.57 ppm: H$_{18}$
5.73 ppm: H$_4$
3.67 ppm: CH$_2$OH
6.65 and 7.02 ppm: aromatics

STEP C: (17S)
11β-[4-(dimethylamino)-phenyl]-3',4',5',6'-tetrahydro-spiro (Δ$^{4,9}$-estradien-17,2' (2H) pyran)-3-one A solution of 788 mg of the product of Step B and 15 ml of anhydrous pyridine was cooled to 0° C. and 1.5 g of tosyl chloride were added. The mixture was stirred for one hour at ambient temperature and 30 ml of ice were added. then the mixture was neutralized with 14.5 ml of concentrated hydrochloric acid and the aqueous phase was extracted with methylene chloride, dried and evaporated to dryness. The residue was purified by passage through silica and elution with methylene chloride-acetone (95–5) to obtain 0.2 g of the expected product.

NMR Spectrum (CDCl$_3$) 2.90 ppm: H of dimethylamino
4.30 ppm: H$_{11}$
0.53 ppm: H$_{18}$
3.46 and 3.74 ppm: —CH$_2$O
5.74 ppm: H$_4$
7.02 and 6.64 ppm: aromatics

EXAMPLE 4
(17S) 11β-[4-(dimethylamino-phenyl]-spiro (Δ$^{4,9}$-estradien-17,2'-oxiran)-3-one Using the procedure of Step B of Example 2, 2.42 g of cyclic (1,2-ethanediyl) acetal of 11β-[4-(dimethylamino)-phenyl]-spiro ($\Delta^9$-estrene-17,2'-oxiran)-5α,-ol-3-one and Amberlite IRC 84 resin were reacted. After cooling, the resin was filtered, rinsed with 60 ml of ethanol and evaporated to dryness. The residue was triturated in 30 ml of isopropyl ether and stirred at 40° C. After chilling, separating, rinsing with isopropyl ether and drying under reduced pressure, 0.844 g of the expected product were obtained. A further 0.273 g of product were recovered from the mother liquors which melted at 228° C. After purification by chromatography on silica [eluent:cyclohexane-ethyl acetate (70–30)], 0.750 g of product were obtained from the first lot melting at 234° C. and having a specific rotation of $[\alpha]_D = +270°$ C.±3.5° C. (c=0.5% CHCl$_3$).

NMR Spectrum (CDCl$_3$)
2.92 ppm: H of dimethylamino
5.8 ppm: H$_4$
4.33 ppm: H$_{11}$
0.6 ppm: H$_{18}$
2.63 and 2.98 ppm: H of oxirane
6.67 and 7.01 ppm: aromatics

EXAMPLE 5

(17S) 11β-[4-(methylthio-phenyl]-spiro-($\Delta^{4,9}$-estradien-17,2'-oxiran)-3-one STEP A: Cyclic 3,3-(1,2-ethanediyl)-acetal of 11β-[4-(methylthio)-phenyl]-$\Delta^9$-estrene-5-ol-3,17-diene A mixture of 0.672 g of cupric chloride, 0.212 g of lithium chloride, 165 ml of anhydrous tetrahydrofuran and 16.5 g of cyclic 3,3-(1,2-ethanediyl)-acetal of 5α,10α-epoxy-$\Delta^{9(11)}$-estrene-3,17-dione was cooled at −6° C. and 100 ml of a 0.75M solution of 4-(methylthio)-phenyl magnesium bromide was added dropwise over 75 minutes. The mixture was stirred under inert atmosphere at −10° C. for one hour and 100 ml of a saturated ammonium chloride solution were added with stirring for 10 minutes. Extraction with ethyl acetate was effected and the extracts were washed with water, dried and concentrated to dryness under reduced pressure. The residue was taken up in a small amount of hexane, separated and washed with hexane. After drying under reduced pressure at 60° C. for one hour, 22.2 g of crude product were obtained melting at 202° C.

After chromatography on silica eluent:cyclohexane-ethyl acetate (1—1)+0.001 triethylamine), and crystallization from ethyl acetate, the product was obtained melted at 209° C.

STEP B: (17S) cyclic (1,2-ethanediyl)-acetal of 11β-[4-(methylthio)-phenyl]-spiro ($\Delta^9$-estrene-17,2'-oxiran)-3-one 12.7 ml of a 0.9M solution of potassium tert-butylate, 22 ml of tetrahydrofuran and 27 ml of anhydrous dimethylsulfoxide were cooled to 5° C. and 2.20 g of trimethyl sulfonium iodide were added over a few minutes, with stirring for 30 minutes at 5° C. Then, 2.45 g of the product of Step A were poured into 30 ml of anhydrous tetrahydrofuran at 5° C. over 7 minutes, and the mixture was stirred for one hour at 0° C. to +5° C. The mixture was poured into 300 ml of water and was extracted with ethyl acetate. The extracts were washed with a saturated aqueous sodium chloride solution, dried and evaporated to dryness. the residue was taken up in 15 ml of ethyl ether, chilled, separated, trieturated with a minimal amount of cold ethyl ether and dried under reduced pressure to obtain 2.1 g of the expected product melting at 130° C.(inst.)

| IR Spectrum (CHCl$_3$) | |
|---|---|
| OH: | 3508 cm$^{-1}$ |
| Aromatics: | 1592 cm$^{-1}$ |
| | 1555 cm$^{-1}$ |
| | 1493 cm$^{-1}$ |

STEP C: (17S) 11β-[4-(methylthio-phenyl]-spiro ($\Delta^{4,9}$-estradien-17,2'-oxiran)-3-one 2.1 g of the product of Step B were dissolved in 100 ml of ethanol under inert atmosphere and 4.2 g of Amberlite IRC 84 resin (Rohm and Haas) were added. The mixture was refluxed for 15 hours and 30 minutes. After cooling, the mixture was filtered and washed with ethanol and the filtrate evaporated. After being kept cold for one hour, the product was separated and triturated with a minimal amount of cold ethanol and dried under reduced pressure to obtain 0.49 g of the expected product melting at 121°–122° C. After crystallization from an ethanolmethylene chloride mixture (4–5), the product melted at 122° C. then 167° C.

| UV Spectrum (EtOH) MW 406.6 | |
|---|---|
| Max. 259 nm | ε = 15.700 |
| Max. 300 nm | ε = 18.700 |

NMR Spectrum (CDCl$_3$)
2.43 ppm: CH$_3$S
5.76 ppm: H$_4$
4.32 ppm: H$_{11}$
0.55 ppm: H$_{18}$
2.61 and 2.94 ppm: H of oxirane
7.02 and 7.13 ppm: aromatics PHARMACOLOGICAL STUDY Study of the activity of the products of the invention on hormone-receptors:

A. Progestogene receptor of the uterus of a rabbit:

Impuberal female rabbits of about 1 kg received a cutaneous application of 25 g of estradiol and, 5 days after this treatment, the animals were killed. The uteri were removed, weighted and homogenized at 0° C. in a Potter teflon-dish in a buffered solution TS (Tris 10 mM, saccharose 0.25M, HCl pH 7.4) (1 g of tissue per 50 ml of TS). The homogenate was then ultra-centrifuged (105,000 g×90 minutes) at 0° C. and aliquots of the supernatant thus obtained were incubated at 0° C. for a time t, with a constant concentration (T) of tritiated product R (17,21-dimethyl-19-nor-$\Delta^{4,9}$-pregnadien-3,20-dione) in the presence of increasing concentrations (0–2500×10$^{-9}$M) either of cold R, or of cold progesterone or of the cold product under test. The concentration of bonded tritiated R (B) each incubate by the technique of adsorption on dextran carbon.

B. Glucocorticoid receptor of the thymus of a rat:

Sprague-Dawley EPOS male rats weighting 160 to 200 g were suprarenalectomized and, 4 to 8 days after this removal, the animals were killed. The thymuses were removed and homogenized at 0° C. in a buffer Tris 10 mM, saccharose 0.25M, dithiothreitol 2 mM, HCl, pH 7.4, with Potter polytetrafluoroethylene-dish (1 g of tissue per 10 ml of TS). The homogenate was then ultracentrifuged (105,000 g×90 minutes) at 0° C. Aliquots of the supernatant thus obtained were incubated at 0° C. for a time t, with a constant concentration (T) of tritiated dexamethasone in the presence of increasing concentrations ($0-2500 \times 10^{-9}$M) either of cold dexamethasone, or of cold product under test. The concentration of bonded tritiated hexamethasone (B) was then measured in each incubate by the technique of adsorption on dextran carbon.

Calcultion of the relative bond affinity:

The calculation of the relative bond affinity (RBA) was the same for all the receptors. The following 2 curves were drawn: the percentage of bonded tritiated hormone B/T as a function of the logarithm of the concentration of the cold reference hormone and B/T as a function of the logarithm of the concentration of the cold product under test. The straight line of the equation $I_{50} = (B \max/T + B \min/T)/2$ was determined. B/T max = percentage of bonded tritiated hormone for an incubation of this hormone tritiated at a concentration (T). B/T min = percentage of bonded tritiated hormone for an incubation of this tritiated hormone at a concentration (T) in the presence of a large excess of cold hormone ($2500 \times 10^{-9}$M). The intersections of the straight line $I_{50}$ and the curves enables the concentrations of cold reference hormone (CH) and of cold product under test (CX) which inhibit by 50% the bond of the tritiated hormone on the receptor to be evaluated. The relative bond affinity (RBA) of the product tested was determined by the equation:

$$RBA = 100(CH)/(CX)$$

The results obtained are the following:

| Products of examples | Incubation Time at 0° C. | | | |
|---|---|---|---|---|
| | Progestogene | | Glucocorticoid | |
| | 2 H | 4 H | 2 H | 4 H |
| 1 | 93 | 415 | 126 | 43 |
| 2 | 23 | 67 | 56 | 22 |
| 3 | 24 | 157 | 23 | 24 |

Conclusion:

The products studied, particularly the product of Example 1, showed a marked affinity for glucocorticoid and progestogen receptors. From the results obtained, it can be concluded that the products offer agonistic or antagonistic activities for glucocorticoids and progestogens.

C. Antiglucocorticoid activity:

The technique used was derived from the method described by Dausse et al in Molecular Pharmacology, Vol. 13, p. 948 to 955 (1977) ("The Relationship Between Glucocorticoid Structure and Effects upon Thymocytes"), for thymocytes of mice.

Thymocytes of suprarenalectomized rats were incubated at 37° C. for 3 hours in a nutritive medium containing $5.10^{-8}$M of dexamethasone in the presence or absence of a product test at various concentrations. Tritiated uridin was added and incubation was continued for one hour. The incubates were cooled, treated with a 5% solution of trichloroacetic acid, filtered on Whatman GF/A paper and washed three time with a 5% solution of trichloroacetic acid. The radioactivity retained by the filter was determined. Glucocorticoids and, in particular dexamethasone, cause a decrease in the incorporation of tritiated uridin. The products of Examples 1 to 4 oppose this effect.

| Product of example | $5.10^{-8}$ M dexamethasone and the product under test at a concentration of | % inhibition of the effect of dexamethasone |
|---|---|---|
| 1 | $10^{-8}$ M | 16 |
| | $10^{-7}$ M | 55 |
| | $10^{-6}$ M | 122 |
| 2 | $10^{-8}$ M | 10 |
| | $10^{-7}$ M | 27 |
| | $10^{-6}$ M | 76 |
| 3 | $10^{-8}$ M | 7 |
| | $10^{-7}$ M | 22 |
| | $10^{-6}$ M | 93 |

It has been noted in addition that, used by themselves the products tested do not cause any glucocorticoid-type effect.

Conclusion:

The products studied showed a very marked antiglucocorticoid activity while having no of glucocorticocoid activity.

D. Abortive activity in a female rat:

Day $D_1$ of gestation was determined by the presence of spermatozoids in the vaginal smear and, on day $D_9$ of the gestation, the product was administered in suspension in carboxymethyl cellulose containing 0.5% Tween. The animals were killed 72 hours after the treatment and the uterus was examined to determine the state of gestation. A complete abortion in all the animals of the group was noted with the product of Example 1 administered at a dose of 3 mg/kg.

Various modifications of the compounds and methods of the invention may be made without departing from the spirit or scope thereof and it is to be understood that the invention is intended to be limited only by the appended claims.

What we claim is:

1. A compound of the formula

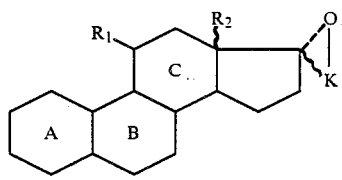

I wherein $R_1$ is selected from the group consisting of phenyl, benzyl, thienyl, furyl, isothienyl, isofuryl, thiazolyl, isothiazolyl, oxazolyl, isoxazolyl, thiadiazolyl, pyridinyl and piperidinyl unsubstituted or substituted with at least one member of the group consisting of (a) haloalkyl, alkyl and alkoxy of 1 to 8 carbon atoms, alkenyloxy of 2 to 8 carbon atoms, all unsubstituted or substituted with at least one halogen, (b) —OH, (c) —CF$_3$ (d) acyl of 1 to 6 carbon atoms, (e) carboxy, (f) esterified carboxy, (g) alkylthio and oxidized alkylthio of 1 to 8 carbon atoms, (h) —NH$_2$, (i) mono- and dialkylamino of 1 to 8 carbon atoms and oxidized amino mono- or dialkylamino, (j) morpholino, (k) piperidino, (l) piperazino, (m) dimethylaminomethyl dimethylaminomethyl, dimethylamino ethyl and dimethylamino ethoxy and (n) trimethylsilyl or N-methyl-2,3-dihydro-1H-indol-5-yl, $R_2$ is a hydrocarbon of 1 to 8 carbon atoms in the α- or β-position, the wavy line of the spiro ether indicates the oxygen is α- or β-, X is selected from the group consisting of —CH=CH—CH$_2$—CH$_2$— and —(CH$_2$)$_n$, n is 1, 2 or 4, the rings have a structure selected from the group consisting of

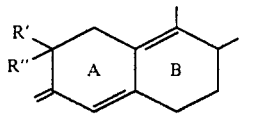

(a)

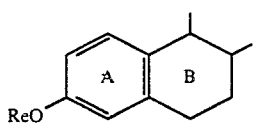

(b)

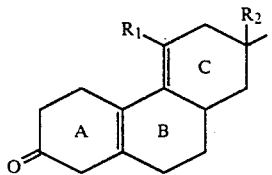

(c)

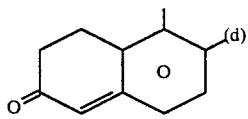

(d)

and

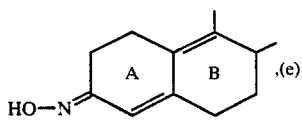

(e)

R' and R" are individually hydrogen or alkyl of 1 to 4 carbon atoms, $R_e$ is selected from the group consisting of hydrogen, alkyl of 1 to 6 carbon atoms and acyl, and non-toxic,k pharmaceutically acceptable acid addition salts of said compound.

2. A compound of claim 1 selected from the group consisting of compounds of the formula

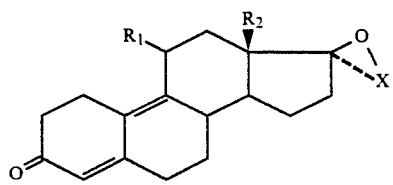

I' wherein $R_1$ is as defined in claim 1, $R_2$, when in the β-position, is hydrocarbon of 1 to 18 carbon atoms, the oxygen atom of the spiro ether is in the 17β-position, X is —(CH$_2$)$_n$—, or —CH=CH—CH$_2$—CH$_2$—, n is 2 or 4 and non-toxic, pharmaceutically acceptable salts of said compound.

3. The compound of claim 1 wherein $R_1$ is phenyl or benzyl having an amino group

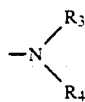

in which each of $R_3$ and $R_4$ is a primary, secondary or tertiary alkyl of 1 to 8 carbon atoms or $R_3$ and $R_4$ form, together with the nitrogen atom to which they are attached, piperazinyl, piperidinyl or morpholino or phenyl substituted with a methylthio or ethylthio and non-toxic, pharmaceutically acceptable salts of the compound.

4. The compound of claim 1 wherein $R_1$ is phenyl with a p-substituent.

5. The compound of claim 1 wherein $R_1$ is selected from the group consisting of

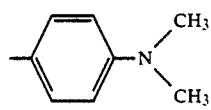

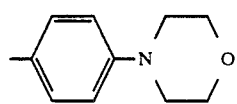

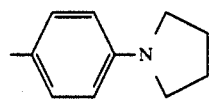

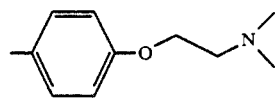

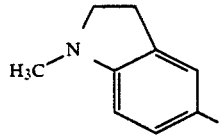

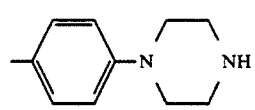

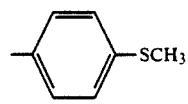

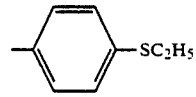

and

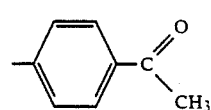

-continued

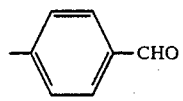

and their non toxic pharmaceutically acceptable salts.

6. The compound of claim 1 wherein $R_1$ is

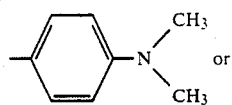
or
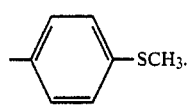

7. A compound of claim 1 selected from the group consisting of (17R) 11β-[4-(dimethylamino)-phenyl]-spiro ($\Delta^{4,9}$-estradien-17,2'-oxetan)-3-one, (17R) 11β-[4-(methylthio)-phenyl]-spiro ($\Delta^{7,9}$-estradien-17,2'-oxetan)-3-one and their non-toxic, pharmaceutically acceptable salts.

8. A compound of the formula

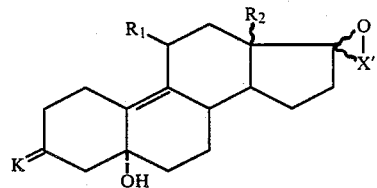

wherein $R_1$, $R_2$ are as defined in claim 1, K is a keto protective group and X' is $-(CH_2)_{nl}-$ or $-CH=CH-CH_2-CH_2$, nl is 2 or 4.

9. An antiandrogenic composition comprising an antiandrogenically effective amount of at least one compound of claim 1 and an inert pharmaeutical carrier.

10. The composition of claim 9 wherein the active comound is selected from the group consisting of compounds of the formula

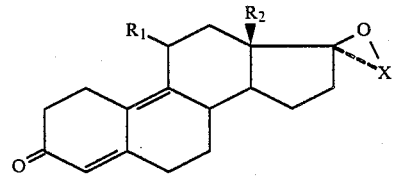

wherein $R_1$ is as defined in claim 1, $R_2$ when in the β-position, is a hydrocarbon of 1 to 18 carbon atoms, the oxygen atom of the spiro ether is in the 17β-position, X is $-(CH_2)_n-$, or $-CH=CH-CH_2-CH_2-$, n is 2 or 4 and non-toxic, pharmaceutically acceptable salt of said compound.

11. The composition of claim 9 wherein the active compound is phenyl or benzyl having an amino group

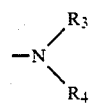

in which each of $R_3$ and $R_4$ is a primary, secondary or tertiary alkyl of 1 to 8 carbon atoms or $R_3$ and $R_4$ form, together with the nitrogen atom to which they attached, piperazinyl, piperidinyl or morpholino or phenyl substituted with a methylthio or ethylthio and non-toxic, pharmaceutically acceptable salts of said compound.

12. The composition of claim 9 wherein the active compound is phenyl with a p-substituent.

13. The composition of claim 9 wherein the active compound is selected from the group consisting of

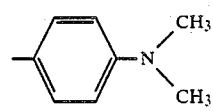

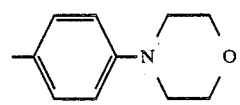

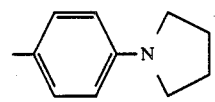

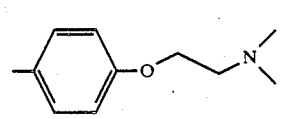

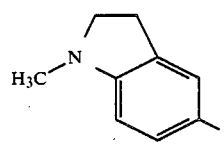

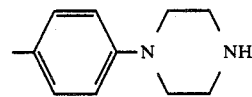

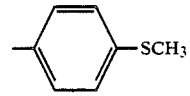

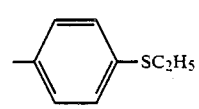

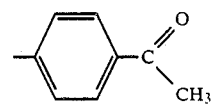

and

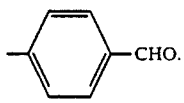

14. The composition of claim 9 wherein the active compound is

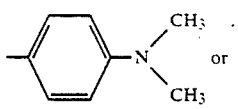

or

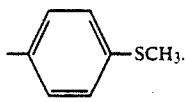

15. The composition of claim 9 wherein said compound is selected from the group consisting of (17R) 11β-[4-(dimethylamino)-phenyl]-spiro ($\Delta^{4,9}$-estradien-17,2'-oxetan)-3-one, (17R) 11β-[4-(methylthio)-phenyl]-spiro ($\Delta^{4,9}$-estradien-17,2'-oxetan)-3-one and their non-toxic, pharmaceutically acceptable salts.

16. A method of inducing antiandrogenic activity in warm-blooded animals comprising administering to said warm-blooded animals an antiandrogenically effective amount of at least one compound of claim 1.

17. A method of claim 16 wherein said compound is of the formula

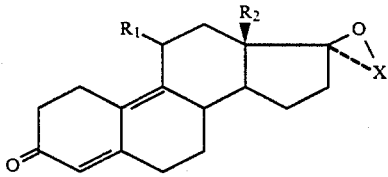

wherein $R_1$ is as defined in claim 1, $R_2$, when in the β-position, is a hydrocarbon of 1 to 18 carbon atoms, the oxygen atom of the spiro ether is in the 17β-position, X is —(CH$_2$)$_n$— or —CH=CH—CH$_2$—CH$_2$—, n is 2 or 4 and non-toxic, pharmaceutically acceptable salts of said compound.

18. The method of claim 16 wherein the active compound is phenyl or benzyl having an amino group in which each of $R_3$ and $R_4$ is a primary, secondary or tertiary alkyl of 1 to 8 carbon atoms or $R_3$ and $R_4$ form, together with the nitrogen atom to which they are attached, piperazinyl, pipeidinyl or morpholino or phenyl substituted with a methylthio or ethylthio and non-toxic, pharmaceutically acceptable salts of said compound.

19. The method of claim 16 wherein the active compound is phenyl with a p-substituent.

20. The method of claim 16 wherein the active compound is selected from the group consisting of

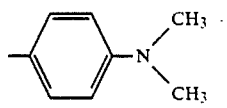

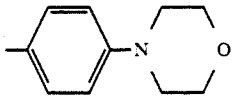

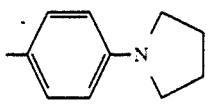

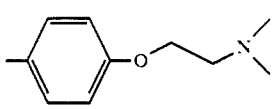

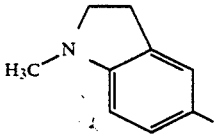

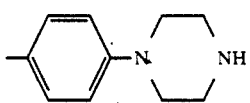

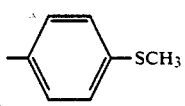

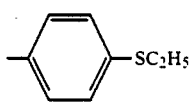

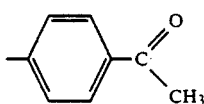

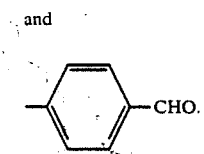

and

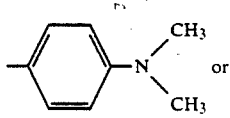

21. The method of claim 16 wherin the active compound is

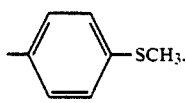

or

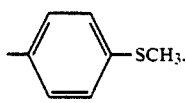

22. The method of calim 16 wherein said compound is selected from the group consisting of (17R) 11β-[4-(dimethylamino)-phenyl]-spiro ($\Delta^{4,9}$-estradien-17,2'-oxetan)-3-one, (17R) 11β-[4-(methylthio)-phenyl]-spiro ($\Delta^{4,9}$-estradien-17,2'-oxetan)-3-one, and their non-toxic, pharmaceutically acceptable salts.

* * * * *

UNITED STATES PATENT AND TRADEMARK OFFICE
CERTIFICATE OF CORRECTION

PATENT NO. : 4,921,846
DATED : May 1, 1990
INVENTOR(S) : LUCIEN NEDELEC, ANDRE CLAUSSNER, DANIEL PHILIBERT and MARTINE MOGUILEWSKY It is certified that error appears in the above-identified patent and that said Letters Patent is hereby corrected as shown below:

| Col. | Line(s) | | |
|---|---|---|---|
| 31 | 5-6 Claim 1 | "-CH=CH-$CH_2$-$CH_2$-" should be | -- -CH=CH-$CH_2$-$CH_2$- -- |
| 33 | 41-42 Claim 8 | "-CH=CH-$CH_2$-$CH_2$-" should be | -- -CH=CH-$CH_2$-$CH_2$- -- |
| 33 | 48 Claim 10 | "comound" should be --compound-- | |

Signed and Sealed this

Twenty-ninth Day of October, 1991

Attest:

HARRY F. MANBECK, JR.

Attesting Officer     Commissioner of Patents and Trademarks